(12) United States Patent
Nho et al.

(10) Patent No.: US 6,858,736 B2
(45) Date of Patent: Feb. 22, 2005

(54) HEXA-ARM POLYETHYLENE GLYCOL AND ITS DERIVATIVES AND THE METHODS OF PREPARATION THEREOF

(75) Inventors: Kwang Nho, Walnut Creek, CA (US); Hyun Chang-min, Seoul (KR); Jung-Hun Lee, Kyonggi-do (KR); In-Kyung Kim, Seoul (KR); Young-Kyoung Pak, Seoul (KR)

(73) Assignee: SunBio, Inc. (KR)

( * ) Notice: Subject to any disclaimer, the term of this patent is extended or adjusted under 35 U.S.C. 154(b) by 0 days.

(21) Appl. No.: 10/326,408

(22) Filed: Dec. 23, 2002

(65) Prior Publication Data

US 2004/0096507 A1 May 20, 2004

(30) Foreign Application Priority Data

Nov. 8, 2002 (KR) .................. 10-2002-0069031

(51) Int. Cl.$^7$ .................. C07D 213/62; C07D 207/40; C07C 69/34; C07C 311/00; C07C 217/00
(52) U.S. Cl. .................. 546/290; 548/545; 556/444; 558/46; 558/267; 560/190; 564/505; 568/420; 568/613
(58) Field of Search .................. 546/290; 548/545; 556/444; 558/46, 267; 560/190; 564/505; 568/420, 613

(56) References Cited

U.S. PATENT DOCUMENTS

| 4,578,525 A | * | 3/1986 | Bruckner .................. 568/918 |
| 5,162,430 A | | 11/1992 | Rhee et al. |
| 5,324,775 A | | 6/1994 | Rhee et al. |
| 5,328,955 A | | 7/1994 | Rhee et al. |
| 5,583,114 A | | 12/1996 | Barrows et al. |
| 5,648,506 A | | 7/1997 | Desai et al. |
| 5,874,500 A | | 2/1999 | Rhee et al. |
| 5,977,163 A | | 11/1999 | Li et al. |
| 6,312,725 B1 | | 11/2001 | Wallace et al. |

OTHER PUBLICATIONS

Leach et al., "Reductionof postoperative adhesions in the rat uterine horn model with poloxamer 407," *Am J Obstet Gynecol,* May 1990, pp. 1317–1319, vol. 162, No. 3.

* cited by examiner

Primary Examiner—Paul A. Zucker
(74) Attorney, Agent, or Firm—Knobbe, Martens, Olson & Bear, LLP

(57) ABSTRACT

The present invention relates to novel hexa-arm polyethylene glycol (6-arm PEG) and its derivatives. The core of 6-arm PEG derivatives is sorbitol and the end groups can be derivatized into many different reactive functionalities that are useful in conjugating with many different targets. The present invention also provides a biodegradable polymeric hydrogel-forming composition comprising the 6-arm PEG and its derivatives, and methods of using such 6-arm PEG derivatives as surgical or biological implants or sealants.

4 Claims, No Drawings

HEXA-ARM POLYETHYLENE GLYCOL AND ITS DERIVATIVES AND THE METHODS OF PREPARATION THEREOF

CROSS REFERENCE TO RELATED APPLICATION

This application is an international patent application, claiming the benefit under 35 USC § 111(a) of Korean Patent Application No. 10-02-69031 (KR10-02-69031), which was filed on Nov. 8, 2002.

FIELD OF THE INVENTION

This invention relates to novel hexa-arm polyethylene glycol (6-arm PEG) and its derivatives and the preparation thereof. The present invention provides a biodegradable polymeric hydrogel-forming composition comprising 6-arm PEG and its derivatives, and the uses thereof.

BACKGROUND OF THE INVENTION

The human genome consisted of DNA polymers having an enormous amount of information which is not capable of being substituted with general synthetic compounds. In the last decade, progress in recombinant DNA technologies has enabled remarkable discovery and/or production of a large number of physiologically active proteins and many of them with therapeutic potential have been used as biopharmaceuticals. Where certain diseases and the damage of organs are not treatable with natural recovery, the use of artificial material based on a high molecular weight polymer can be very useful. Moreover, most of these medical polymer materials may provide with better biocompatibility, suitability, and pharmacokinetics than conventional material. The use of polymer compositions, particularly, consisting of synthetic polymer in the field of medical and biotechnology. In contrast to most of naturally derived compositions, synthetic polymer compositions can be formulated to exhibit predetermined physical characteristics such as gel time, gel strength, as well as biological characteristics such as degradability. Among these polymer, polyethylene glycol (PEG) and its derivatives has been used most frequently for implants or sealants by means of its non-immungenic and hydrophilic characteristics.

Polyethylene glycol (PEG) is amphiphilic that is soluble not only in water but also in organic solvents. Therefore, even poorly soluble material in water can be converted to possess hydrophilicity when conjugated with PEG. PEG is known to be weakly immunogenic and almost nontoxic to human, thus can be useful in a number of clinical applications. When a PEG conjugate is administered to biological systems, characteristics of extended residence time and reduced rate of renal clearance are often observed. For examples, U.S. patents (U.S. Pat. No. 5,977,163 and U.S. Pat. No. 5,648,506) described PEG-taxol conjugates wherein the taxol is used for a pharmaceutical treatment for ovarian and mammaian cancers. While taxol is known to be extremely water insoluble to make it difficult to be formulated as a parenteral, the PEG-taxol, a PEG-conjugated form of taxol, demonstrated improved water solubility more than 1000 times than that of natural taxol.

In general, PEG is a linear polymer with the hydroxyl group at the terminals. The chemical structure of PEGs is $HO-CH_2CH_2O-(CH_2CH_2O)_n-CH_2CH_2OH$ (PEG) or $CH_3O-CH_2CH_2O-(CH_2CH_2O)_n-CH_2CH_2OH$ (methoxy PEG). The linear PEGs having just one or two end groups, have limited reactivity. However, if a larger number of end groups per PEG molecule, their reactivity will be remarkably improved. To obtaining PEGs having more terminals, their structure has to take up the form of the PEG wherein multiple PEG arms are produced from one single core. For example, U.S. Pat. No 6,312,725 B1 discloses a 4-arm PEG prepared by common and commercially available ethylene oxide addition reaction using pentaerythritol as the core of star PEG. Preparation of 12-arm PEG, the 4-arm sulfhydryl PEGs have to be conjugated with the 4 ends of the pentaerythritol prior to make a core with 12 ends. However, there has not been suggested or disclosed of 6-arm PEG in above reference cited herein.

PEG has been applied for a variety of applications in the biotechnology field. Block copolymers of Pluronic® and Poloxamer® insoluble in cold water in nature are formed into insoluble hydrogels at body temperature when administered into human body (Leach, et al., *Am. J. Obstet. Gynecol.*, 162, pp1317–1319, 1990). Polymerizable cyanoacrylates have been also described for use as tissue adhesives (Ellis, et al., *J. Otolaryngol.*, 19, pp68–72, 1990). In yet another approach, two-part synthetic polymer compositions have been described that they, when mixed together, form covalent bonds with one another, as well as with exposed tissue surfaces (PCT WO 97/22371, which corresponds to U.S. application Ser. No. 08/769,806 U.S. Pat. No. 5,874,500). In a similar approach involving a two-part composition, the mixture of protein and bifuntional crosslinking agent has been described for use as a tissue adhesive (U.S. Pat. No. 5,583,114).

U.S. Pat. No. 5,162,430, issued Nov. 10, 1992 to Rhee et al., and commonly owned by the assignee of the present invention, discloses collagen-synthetic polymer conjugates prepared by covalently binding collagen to synthetic hydrophilic polymers such as various derivatives of polyethylene glycol.

Commonly owned U.S. Pat. No. 5,324,775, issued Jun. 28, 1994, to Rhee et al., discloses various insert, naturally occurring, biocompatible polymers (such as polysaccharides) covalently bound to synthetic, non-immunogenic and hydrophilic polyethylene glycol polymers.

Commonly owned U.S. Pat. No. 5,328,955, issued July 12, to Rhee et al., discloses various activated forms of polyethylene glycol and various linkages which can be used to produce collagen-synthetic polymer conjugates having similar range of physical and chemical properties each other.

Commonly owned, copending U.S. application Ser. No. 08/403,358, filed Mar. 14, 1995, discloses a crosslinked biomaterial composition prepared by using a hydrophobic crosslinking agent, or a mixture of hydrophilic and hydrophobic crosslinking agents. Preferred hydrophobic crosslinking agents include any hydrophobic polymer that contains or can be chemically modified to contain two or more succinimidyl groups.

Commonly owned, copending U.S. application Ser. No. 8/403,360, filed Mar. 14, 1995, discloses a composition useful in the prevention of surgical adhesions comprising a substrate material and an anti-adhesion binding agent; where the substrate material preferably comprises collagen and the binding agent preferably comprises at least one tissue-reactive functional group and at least one substrate-reactive functional group.

Commonly owned, U.S. application Ser. No. 08/476,825, filed Jun. 7, 1995, by Rhee et al., discloses bioadhesive compositions comprising collagen crosslinked with a multifunctionally activated synthetic hydrophilic polymer, as well as methods of using such compositions to effect the adhesion between the first surface and the second surface, wherein at least one of the first and second surfaces is preferably a native tissue surface.

Japanese patent publication No. 07090241 discloses a composition used for temporary adhesion of a lens material to a support, to mount the material on a machining device, comprising a mixture of PEG having an average molecular weight in the range of 1000–5000 D and poly-N-vinylpyrrolidone having an average molecular weight in the range of 30,000–200,000 D.

West and Hubbell disclose the prevention of post-operative adhesions using a photopolymerized PEG-co-lactic acid diacrylate hydrogel and a physically crosslinked PEG-co-polypropylene glycol hydrogel, Poloxamer 407.RTM® (West and Hubbell, *Biomaterials*, 16, pp1153–1156, 1995).

U.S. Pat. No. 5,874,500 disclosed polymeric compositions comprising a group of synthetic polymers containing multiple nucleophilic groups and another group of synthetic polymers containing multiple electrophilic groups and the methods for using these compositions to affect adhesion between the first surface and the second surface wherein at least one of the surfaces is preferably a native tissue surface, which can be used to bring about the augmentation of tissue, or to prevent surgical adhesion, or to coat surfaces of synthetic implants, or to deliver drugs or other active agents, or for ophthalmic applications. The use of polymeric compositions with biological materials such as hydrogel of polymer-collagen, may be useful as bioadhesives in place of surgical sutures or for use in ophthalmic application. In transplantation of skin or cells under clinical situation, the composition can be used as the matrix housing the transplant cells or connecting the skin. These polymeric compositions can also be used as a large space-filling device for organ displacement in a body cavity during surgical or radiation procedures, for example, to protect the intestines from a planned course of radiation to the pelvis.

Each publication cited above and herein is incorporated herein by reference in its entirety to describe and disclose the subject matter for which it is cited.

The present inventors have endeavored to synthesize a novel 6-arm PEG and its derivatives, and finally completed that the biodegradable composition comprising synthetic polymers which contain multiple nucleophilic groups using synthetic polymers containing multiple electrophilic groups, and the methods for using these compositions to effect the augmentation of tissue, or to prevent surgical adhesion, or to coat surfaces of synthetic implants.

SUMMARY OF THE INVENTION

In some embodiments of the invention, a novel hexa-arm polyethylene glycol (6-arm PEG) and its derivatives are provided.

In an additional embodiment of the invention, a biodegradable polymer hydrogel-forming composition comprising the 6-arm PEG and its derivatives is provided.

In further embodiments of the invention, processes for preparing the 6-arm PEG and its derivatives are provided.

DETAILED DESCRIPTION OF THE INVENTION

Accordingly, it is an object of the present invention to provide a novel polyethylene glycol (6-arm PEG) and its derivatives. The core of 6-arm PEG and its derivatives above described is sorbitol and their molecular weight ranges from 100 to 1,000,000, preferably, 1,000 to 100,000 dalton.

It is another object of the present invention to provide a novel hexa-arm polyethylene glycol (6-arm PEG) and its derivatives represented by the following formula (I):

$$
\begin{array}{c}
CH_2O-(CH_2CH_2O)_n-R_1 \\
CH_2O \\
H-C-O-(CH_2CH_2O)_n-R_1 \\
R_1-(OH_2CH_2C)_n-O-C-H \\
H-C-O-(CH_2CH_2O)_n-R_1 \\
H-C-O-(CH_2CH_2O)_n-R_1 \\
CH_2O \\
CH_2O-(CH_2CH_2O)_n-R_1
\end{array}
\tag{I}
$$

wherein, $R_1$ is a hydrogen atom, a hydroxyl group, alkyl group having 1 to 5 carbon atoms, an acrylate group, an acetaldehyde group, an epoxide group, a hydrazide group, a tresylate group, an alkylcarbonyl group or a phenylcarbonyl group having 1 to 10 carbon atoms which substituted by nitro group, primary, secondary or tertiary silane group which substituted by alkyl or alkoxy group having 1 to 5 carbon atoms, glutaric acid group, succinic acid group or $CO(CH_2)_m COONHS$ (I-1), m is an integer of 2 to 3, n is an integer of 20 to 2500.

In a preferred embodiment, the preferred compound is one selected from the group consisting of 6-arm PEG-succinic acid (6-arm PEG-SA), 6-arm PEG-glutaric acid (6-arm PEG-GA), 6-arm PEG-succimidyl succinate (6-arm PEG-SS), 6-arm PEG-succimidyl glutarate (6-arm PEG-SG), 6-arm PEG-nitrophenyl carbonate (6-arm PEG-NPC), 6-arm PEG-silane, 6-arm PEG-acrylate, 6-arm PEG-hydrazide, 6-arm PEG-tresylate, 6-arm PEG-propion aldehyde, 6-arm PEG-tosylate.

It is another object of the present invention to provide a novel 6-arm PEG compound and its derivatives represented by the following formula (II):

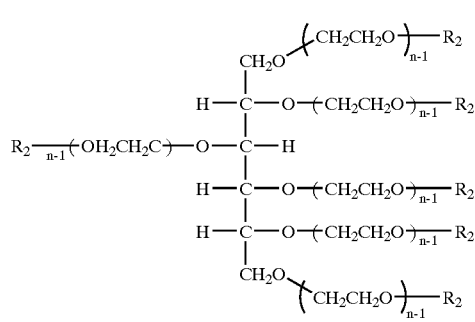

(II)

wherein,
$R_2$ is a hydrogen atom, a hydroxyl group, an isocyanate group, a maleimide group, a o-pyridyl disulfide group, an alkylsulfone, an arylsulfone or a vinylsunfonyl group having 1 to 5 carbon atoms, or an alkyl or an alkene group having 1 to 5 carbon atoms which is substituted or not substituted by amine group, n is an integer of 20 to 2500.

In a preferred embodiment, the preferred compound is one selected from the group consisting of 6-arm PEG-isocyanate,
6-arm PEG-maleimide,
6-arm PEG-orthopyridyl disulfide,
6-arm PEG-vinylsulfone,
6-arm PEG-amine (6-arm PEG-NH$_2$),
6-arm PEG-thiol (6-arm PEG-SH).

The 6-arm PEG and its derivatives of the invention may be chemically synthesized by the methods in the reaction schemes hereinafter, which are merely exemplary and in no way limit the invention. The reaction schemes show the steps for preparing the representative compounds of the present invention, and other compounds also may be produced by following the steps with appropriate modifications of reagents and starting materials, which are envisaged by those skilled in the art. The following schemes and examples are a part of all possible derivatives and are not intended to limit the scope of the invention.

General Synthetic Procedures

Scheme 1

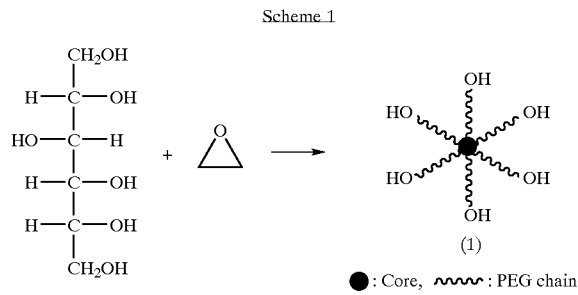

● : Core,  〜〜〜 : PEG chain

As depicted in above Scheme 1, sorbitol is reacted with ethylene oxide to synthesize 6-arm polyethylene glycol (PEG) (1) by polymerization (ethoxylation) of ethylene oxides via a ring-opening reaction. The hexa-arm polyethylene (6-arm PEG) (1) has hydroxyl groups at the terminal of the PEG chains and these hydroxyl groups can be modified into various functional groups such as following schemes and examples.

Scheme 2

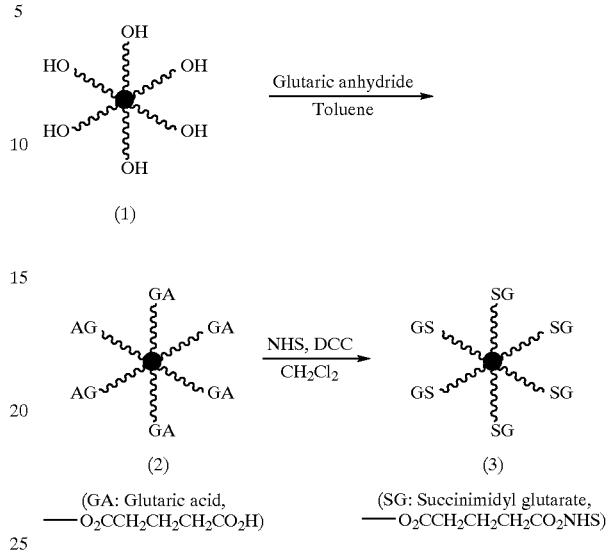

(GA: Glutaric acid, —O$_2$CCH$_2$CH$_2$CH$_2$CO$_2$H)

(SG: Succinimidyl glutarate, —O$_2$CCH$_2$CH$_2$CH$_2$CO$_2$NHS)

As depicted in above Scheme 2, 6-arm PEG (1) synthesized in the Scheme 1 is reacted with glutarate reagents, e.g., glutaric anhydride to synthesize 6-arm PEG-glutatic acid (6-arm PEG-GA) (2). The compound (2) was reacted with N-hydroxy succinimide (NHS) and N,N'-dicyclohexylcarbodiimide (DCC) to produce 6-arm PEG-succinimide glutarate (6-arm PEG-SG) (3).

Scheme 3

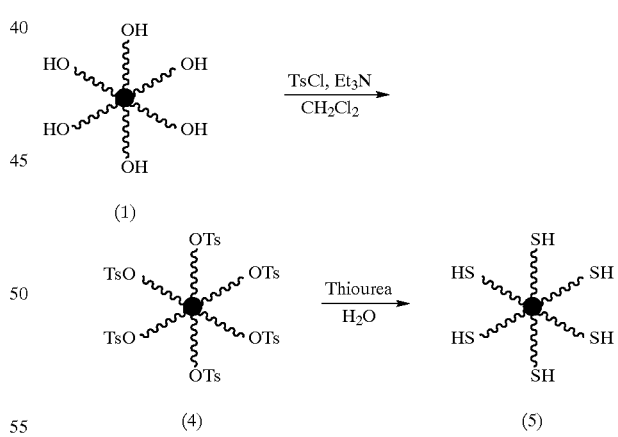

As depicted in above Scheme 3, 6-arm PEG (1) synthesized in the Scheme 1 is reacted with p-toluenesulfonyl chloride (TsCl) and triethylamine (TEA) as reagents, and dichloromethane as solvent to synthesize 6-arm PEG-tosylate (4). The 6-arm PEG-tosylate compound (4) is reacted with thiourea and H$_2$O to produce 6-arm PEG-thiol (6-arm PEG-SH) (5).

Scheme 4

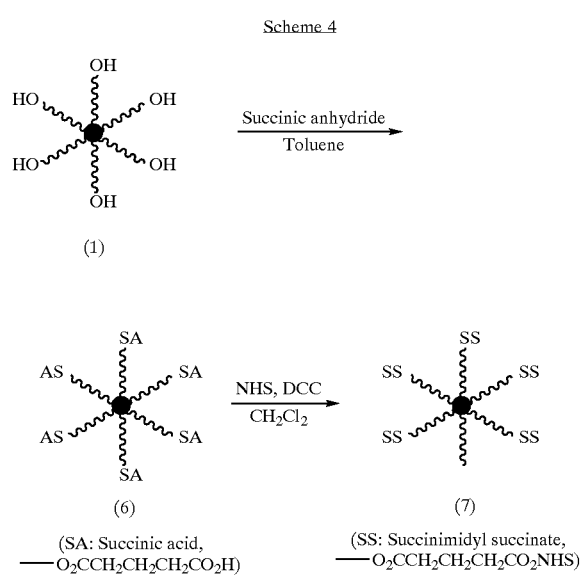

(SA: Succinic acid, —O₂CCH₂CH₂CH₂CO₂H)

(SS: Succinimidyl succinate, —O₂CCH₂CH₂CH₂CO₂NHS)

As depicted in above Scheme 4, 6-arm PEG (1) synthesized in the Scheme 1 is reacted with succinic reagents, e.g., succinic anhydride and toluene as solvent to synthesize 6-arm PEG-succinic acid (6-arm PEG-SA) (6). The 6-arm PEG SA (6) is reacted with N-hydroxy succinimide (NHS) and N, N'-dicyclohexylcarbodiimide (DCC) to produce 6-arm PEG-succinimide succinate (6-arm PEG-SS) (7).

Scheme 5

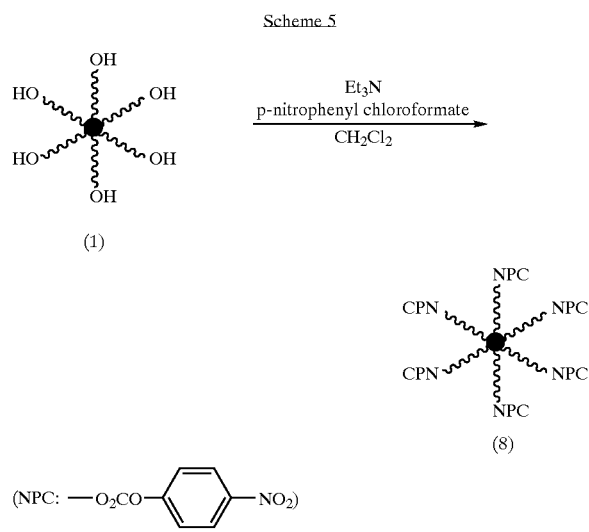

(NPC: —O₂CO—⟨⟩—NO₂)

As depicted in above Scheme, 5, 6-arm PEG (1) synthesized in the Scheme 1 is reacted with p-nitrophenyl chloroformate and TEA as reagents, and dichloromethane as solvent to synthesize 6-arm PEG-nitrophenyl carbonate (6-arm PEG-NPC) (8).

Scheme 6

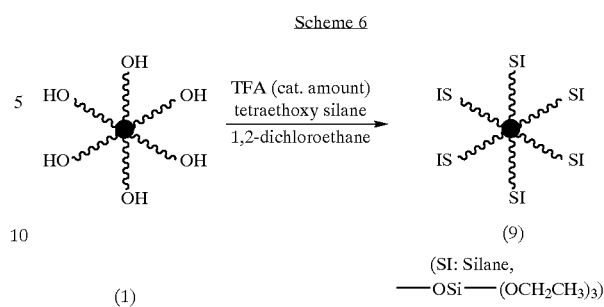

(SI: Silane, —OSi—(OCH₂CH₃)₃)

As depicted in above Scheme 6, 6-arm PEG (1) synthesized in the Scheme 1 is reacted with silanating reagent, e.g., tetraethoxy silane, trifluoroacetic acid (TFA) as a catalyst, and 1,2-dichloroethane as solvent to give 6-arm PEG-silane (6-arm PEG-SI) (9).

Scheme 7

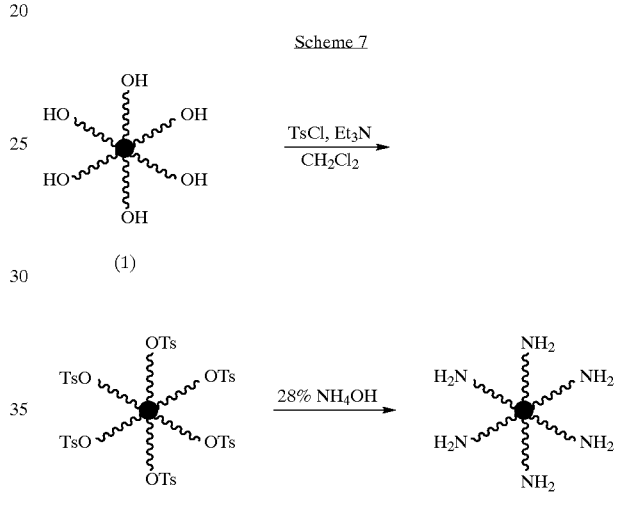

As depicted in above Scheme 7, 6-arm PEG (1) synthesized in the Scheme 1 is reacted with p-TsCl and TEA as reagents and dichloromethane as solvent to give 6-arm PEG-tosylate (4). The 6-arm PEG-tosylate compound (4) is reacted with ammonia water and precipitated with diethyl ether to get 6-arm PEG-amine (10).

It is another object of the present invention to provide a biodegradable polymer hydrogel-forming composition comprising the 6-arm PEG and its derivatives represented by the formula (I) or (II) which can be formed easily by combination with human inner protein or themselves.

A biodegradable polymeric hydrogel-forming composition comprising the 6-arm PEG-SS and 6-arm PEG-SG can be formed easily with albumin, 6-arm PEG-amine or 6-arm PEG-SH etc; the above hydrogel-forming composition comprising the 6-arm PEG-NPC can be formed with albumin or 6-arm PEG-amine etc; the above hydrogel-forming composition comprising the 6-arm PEG-silane can be formed with albumin or 6-arm PEG-amine etc; the above hydrogel-forming composition comprising the 6-arm PEG amine can be formed with 6-arm PEG-SS, 6-arm PEG-SG, 6-arm PEG-silane or 6-arm PEG-NPC etc; the above hydrogel-forming composition comprising the 6-arm PES-SH can be formed with 6-arm PEG-SS or 6-arm PEG-SG etc. The hydrogel which exhibits potent biocompatible activity, can be used as novel material in the biotechnology and medical field.

It is another object of the present invention to provide a method of using the biodegradable polymer hydrogel-forming composition comprising 6-arm PEG and its derivatives as carrier, biological or surgical implant or sealants.

The biodegradable polymeric hydrogel-forming compositions of the present invention can be used in a variety of different pharmaceutical applications. In general, the compositions described herein can be adapted for use in any gel-forming application where synthetic gel matrices are currently being utilized. For example, the compositions of the present invention are useful as tissue sealants, in tissue augmentation, in tissue repair, as hemostatic agents, in preventing tissue adhesions, in providing surface modifications, and in drug/cell/gene delivery applications. One of skill in the art could easily determine the appropriate administration protocol to use with any composition having a known gel strength and gelation time based on the principles described herein and well known scientific principles. A more detailed description of several specific applications is given below.

In a preferred application, the compositions described herein can be used for medical conditions that require a coating or sealing layer to prevent the leakage of gases, liquid or solids. The method entails applying both components to the damaged tissue or organ

- to seal vascular and or other tissues or organs to stop or minimize the flow of blood
- to seal thoracic tissue to stop or minimize the leakage of air
- to seal gastrointestinal tract or pancreatic tissue to stop or minimize the leakage of tissue contents
- to seal bladder or ureters to stop or minimize the leakage of urine
- to seal skin or tissue to stop the leakage of body fluid.

These compositions may also be used to adhere tissues together such as small vessels, nerves or dermal tissue.

A preferred application is a method of reducing the formation of adhesions after a surgical procedure in a patient. The method entails applying the material onto the damaged tissue or organ either by spraying both components together or by applying previously admixed components. The components will react together to form a hydrogel on the tissue surface. The medical procedures include gynecological, abdominal, neurosurgical, cardiac and orthopedic indications.

A preferred application is a method of locally applying a biologically active substance to patients. The active substance can be delivered in conjunction with the two components such that the material can form in situ or as a preformed implant. The active substance can be either released through diffusion controlled processes or may be covalently bound to the components such that it will be released as the resulting hydrogel degrades.

The biologically active substances can be any of a variety of organic and inorganic materials, including proteins, carbohydrates and nucleic acids. Specific examples include enzymes, antibiotics, antineoplastic agents, cytokines, local anesthetics, hormones, antiangiogenic agents, antibodies, neurotransmitters, psychoactive drugs, drugs affecting reproductive organs and therapeutic oligonucleotides.

A preferred application is a method of applying coating to implants to affect the surface properties of implants or to help adhere implant to tissue surfaces. A coat of components may be applied

- to vascular grafts, stents to minimize or stop the leakage of blood or body fluid from these devices
- to catheters or breast implants to reduce or stop excessive fibrosis
- to artificial patches or meshes to minimize excessive fibrosis and to help adhere the implants to tissue surfaces.

Hereinafter, the following formulation methods and excipients are merely exemplary and in no way limit the invention.

The biodegradable polymeric hydrogel-forming composition according to the present invention can be formulated in the form of injection. For example, the composition of the present invention can be injected subcutaneously or intramuscularly as in the form of pharmaceutically acceptable particles with diameter of 0.1 to 1000 $\mu$m, preferably, 0.5 to 200 $\mu$m, most preferably 1 to 150 $\mu$m. Suitable examples of the carriers include physiological saline, corn oil, cotton seed oil, peanut oil, sesame oil, etc., but are not limited to them.

The compounds of the present invention in pharmaceutical dosage forms may be used in the form of their pharmaceutically acceptable salts, and also may be used alone or in appropriate association, as well as in combination with other pharmaceutically active compounds.

The present invention is more specifically explained by the following examples. However, it should be understood that the present invention is not limited to these examples in any manner.

EXAMPLES

Example 1

Synthesis of 6-Arm Polyethylene Glycol (6-Arm PEG) (1)

The sorbitol was added with catalyst in the chamber at 50~80° C. and added with $N_2$ gas for 2~3 times at 80~120° C. The chamber was pressurized at 4 $kg_f/cm^2$ and 110~130° C., kept for 30 minutes, distilled under reduced pressure for 1 hour. The reaction mixture was added slowly with ethylene oxide at 120~130° C. and −0.5$kg_f/cm^2$, aged for 1 hour at reaction temperature. After the end of the aging, the mixture was distilled under reduced pressure for 1 hour, dropped at 80~90° C., neutralized with neutralizing reagent, distilled under reduced pressure for 30 minutes at 90~100° C. and filtered by line filter at 90~100° C. The filtrate was used as sample.

The synthesized compound was determined by its molecular weight and polydispersity index by GPC and MALDI-TOF MASS spectrometer.

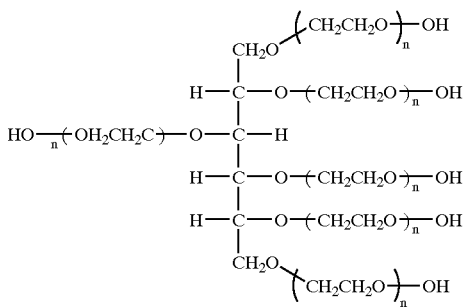

Example 2

Synthesis of 6-Arm PEG-Glutaric Acid (6-Arm PEG-GA) (2)

6-arm PEG (60 g, 0.003 mol, M.W. 20K) was dissolved in 250 Ml of toluene, and glutaric anhydride (10.3 g, 0.09 mol) was added. The reaction mixture was stirred and refluxed for 17 hours. The toluene was evaporated and the crude was dissolved in water and washed two times with ethyl ether. The product was extracted with dichloromethane and the collected organic fraction was dried over $MgSO_4$. The solvent was removed and the product precipitated with ethyl ether. The product was collected by filtration and dried for 12 hours under vacuum to give 58 g of 6-arm PEG-glutaric acid (2).

White solid, $^1$H-NMR ($CDCl_3$) δ: 1.94 ppm (m, 12H,—$CH_2CH_2CH_2$—), 2.41 ppm (m, 24H, —$O_2CCH_2$—, —$CH_2CO_2H$), 3.64 ppm (s, 1818H, PEG backbone, —$OCH_2$—), 4.23 ppm (t, 12H, —$CH_2O_2C$—).

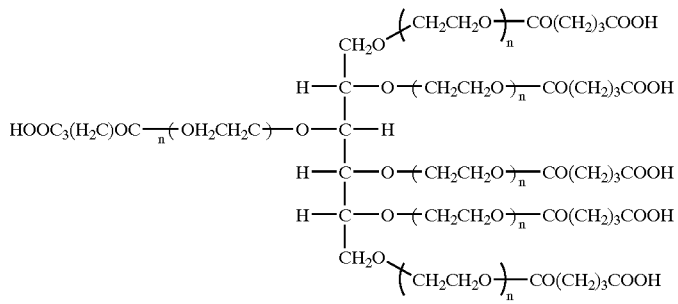

Example 3

Synthesis of 6-Arm PEG-Succinimidyl Glutarate (6-Arm PEG-SG) (3)

6-arm PEG-GA (2) (58 g, 0.0028 mol) and N-hydroxysuccinimide (NHS, 4.0 g, 0.0337 mol) were dissolved in 230 Ml of dichloromethane, and dicyclohexyl carbodiimide (DCC, 6.95 g, 0.0337 mol) in dichloromethane (30 Ml) was dropped slowly. The reaction mixture was stirred for 15 hours at room temperature under nitrogen. The suspension was filtered and the filtrate was precipitated with ethyl ether. The product was collected by filtration and dried for 12 hours under vacuum to give 56 g of 6-arm PEG-succinimidyl glutarate (3).

White solid, $^1$H-NMR ($CDCl_3$) δ: 2.07 ppm (m, 12H,—$CH_2CH_2CH_2$—), 2.49 ppm (t, 12H, —$O_2CCH_2$—), 2.71 ppm (t, 12H, —$CH_2CO_2NUS$), 2.83 ppm (s, 24H, —NHS), 3.64 ppm (s, 1818H, PEG backbone,—$OCH_2$—), 4.24 ppm (t, 12H, —$CH_2O_2C$—)

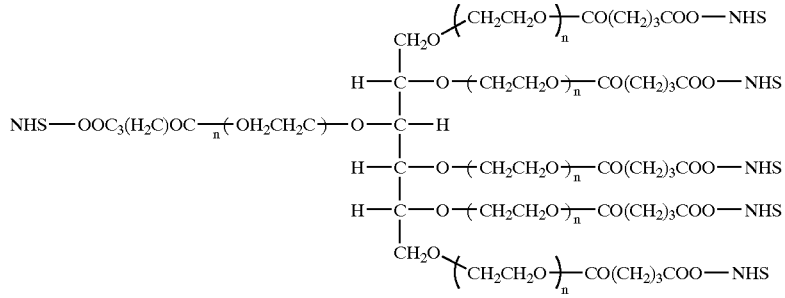

Example 4

Synthesis of 6-Arm PEG-tosylate (4)

6-arm PEG (80 g, 0.004 mol, M.W. 20K) (1) was dissolved in 300 Ml of dichloromethane, and triethylamine (TEA, 20 Ml, 0.144 mol) and p-toluenesulfonyl chloride (TsCl, 23 g, 0.120 mol) were added. The mixture was stirred for 20 hours at room temperature under nitrogen. The solution was filtered, the filtrate was washed two times with saturated $NH_4Cl$ solution and the organic solvent dried over $MgSO_4$. The solvent was removed and the product was precipitated with ethyl ether. The product was collected by filtration and dried for 12 hours under vacuum to give 77 g of 6-arm PEG-tosylate (4).

White solid, $^1$H-NMR (CDCl$_3$) δ: 2.45 ppm (s, 18H, —CCH$_3$), 3.64 ppm (s, 1818H, PEG backbone,—OCH$_2$—), 4.24 ppm (t, 12H, —CH$_2$OTs), 7.35–7.79 ppm (d, 24H, aromatic ring)7

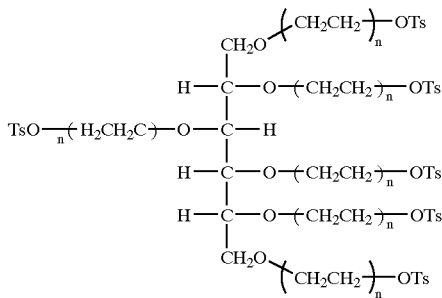

Example 5
Synthesis of 6-Arm PEG-thiol (6-Arm PEG-SH) (5)

6-arm PEG tosylate (4) (77 g, 3.68 mmol, M.W. 20,924,) and thiourea (34 g, 442 mmol) were dissolved in water and the reaction mixture was stirred, refluxed for 20 hours, added with 500 Ml of 1N NaOH solution and refluxed for 2 hours. The reaction mixture was cooled, quenched by saturated NH$_4$Cl solution, extracted two times with dichloromethane and the collected organic fraction was dried over MgSO$_4$. The solvent was removed and the product was precipitated with ethyl ether, collected by filtration and dried for 12 hours under vacuum to obtain 74 g of 6-arm PEG-thiol (5).

White solid, $^1$H-NMR (CDCl$_3$) δ: 1.60 ppm (t, 6H, —SH), 2.70 ppm (q, 12H, —CH$_2$SH), 3.64 ppm (s, 1818H, PEG backbone,—OCH$_2$—)

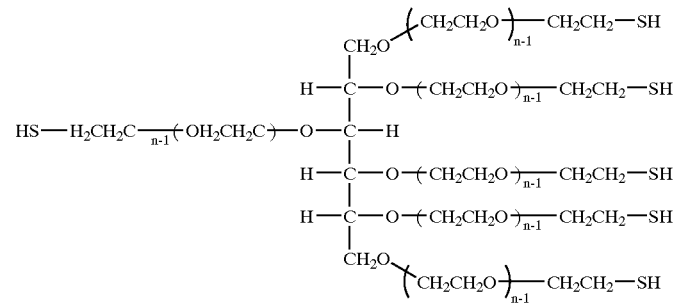

Example 6
Synthesis of 6-Arm PEG-succinic Acid (6-Arm PEG-SA) (6)

6-arm PEG (60 g, 0.003 mol, M.W. 20K) was dissolved in 250 Ml of toluene, and succinic anhydride (9.1 g, 0.09 mol) was added. The reaction mixture was stirred and refluxed for 17 hours. The reaction mixture was distilled under reduced pressure to remove solvent and the remaining residue was dissolved in water and washed two times with ethyl ether. The product was extracted with dichloromethane and the collected organic fraction was dried over MgSO$_4$. The product was precipitated with ethyl ether, collected by filtration and dried for 12 hours under vacuum to get 58 g of 6-arm PEG-succinic acid (6).

White solid,
$^1$H-NMR (CDCl$_3$) δ: 2.64 ppm (m, 24H, —O$_2$CCH$_2$—, —CH$_2$CO$_2$H), 3.64 ppm (s, 1818H, PEG backbone,—OCH$_2$—), 4.26 ppm (t, 12H, —CH$_2$O$_2$C—)

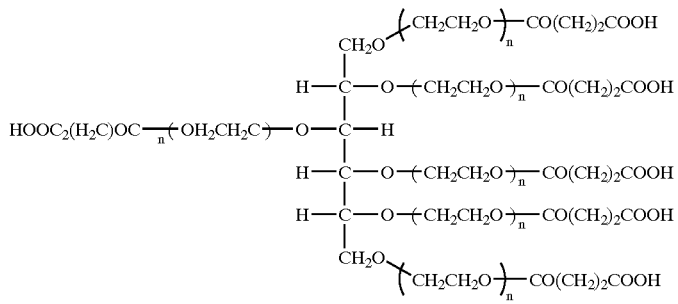

Example 7
Synthesis of 6-Arm PEG-succinimidyl Succinate (6-Arm PEG-SS) (7)

6-arm PEG-SA (6) (58 g, 0.0028 mol) and N-hydroxysuccinimide (NHS, 4.0 g, 0.0337 mol) were dissolved in 230 Ml of dichloromethane, and dicyclohexyl carbodiimide (DCC, 7.0g, 0.0338mol) in dichloromethane ( 30 Ml) was dropped slowly. The reaction mixture was stirred for 15 hours at room temperature under nitrogen. The suspension was filtered and the filtrate was precipitated with diethyl ether, collected by filtration and dried for 12 hours under vacuum to obtain 57 g of 6-arm PEG-succinimidyl succinate (7).

White solid, $^1$H-NMR (CDCl$_3$) δ: 2.77 ppm (t, 12H, —O$_2$CCH$_2$—), 2.83 ppm (s, 24H, —NHS), 2.96 ppm (t, 12H, —CH$_2$CO$_2$NHS), 3.64 ppm (s, 1818H, PEG backbone, —OCH$_2$—), 4.27 ppm (t, 12H, —CH$_2$O$_2$C—)

White solid, $^1$H-NMR (CDCl$_3$) δ: 3.64 ppm (s, 1818H, PEG backbone,—OCH$_2$—), 4.44 ppm (t, 12H, —CH$_2$OCO$_2$—), 7.40–7.28 ppm (d, 24H, aromatic ring)

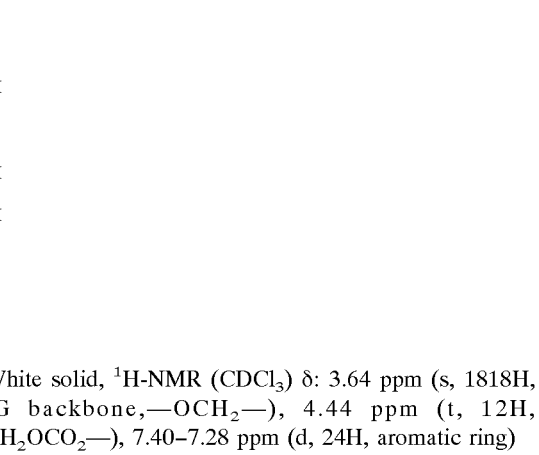

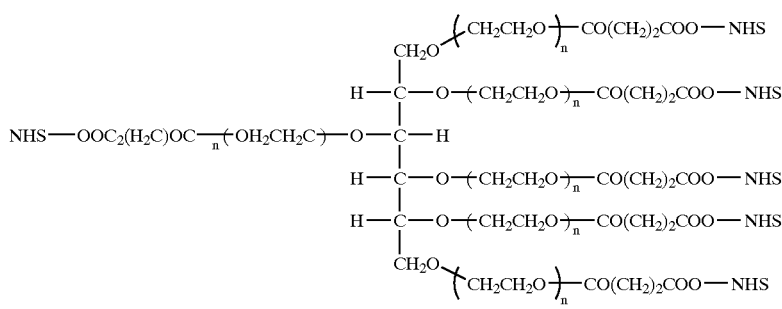

Example 8
Synthesis of 6-Arm PEG-nitrophenyl Carbonate (6-Arm PEG-NPC) (8)

A 6-arm PEG (100 g, 0.005 mol, M.W. 20K) (1) was dissolved in toluene and the solution was distilled to remove humidity and dried. A dried 6-arm PEG was dissolved in 400 Ml of dichloromethane, and triethylamine (10.5 Ml, 0.075 mol) and p-nitophenyl chloroformate (NPC, 12.1 g, 0.06 mol) were added. The reaction mixture was stirred for 24 hours at room temperature. The solution was filtered to remove salt and the filtrate solution was precipitated with ethyl ether, collected by filtration and dried for 12 hours under vacuum to obtain 94 g of 6-arm PEG-nitrophenyl carbonate (8).

-continued

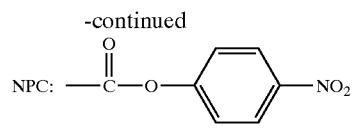

Example 9
Synthesis of 6-Arm PEG-silane (6-Arm PEG-SI) (9)

At 6-arm PEG (60 g, 3 mmol, M.W. 20K) (1) was dissolved in toluene and the solution was distilled to remove humidity and dried. A solution of 6-arm PEG in 1,2-dichloroethane was added with tetraethoxysilane (12.6 Ml, 90 mmol, 30 eq) and a catalytic amount of trifluoroacetic acid (TFA) and the reaction mixture was stirred for 24 hours at 94~96° C. The solvent was removed and the product was precipitated with ethyl ether, collected by filtration and dried for 12 hours under vacuum to get 57 g of 6-arm PEG-silane (9).

White solid, $^1$H-NMR (CDCl$_3$) δ: 2.24 ppm (t, 54H, —CH$_3$), 3.64 ppm (s, 1818H, PEG backbone,—OCH$_2$—), 3.85 ppm (q, 36H, —SiOCH$_2$—)

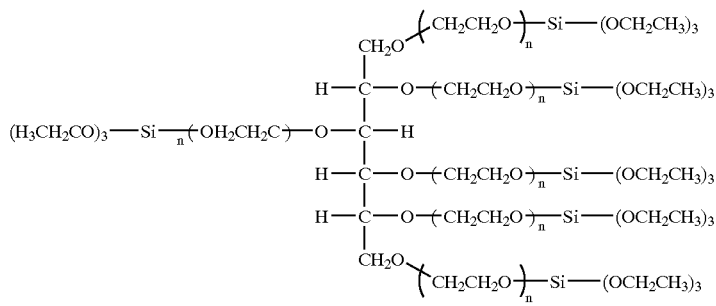

Example 10
Synthesis of 6-Arm PEG-amine (10)

A 6-arm PEG-tosylate (4) 77 g (0.0037 mol) synthesized in the Example 4 was dissolved in 28%-ammonia water (400 Ml) and the solution was reacted for 48 hours. The reaction mixture was extracted two times with dichloromethane and the extract was dried over $MgSO_4$ and filtered to remove the solvent. The product was precipitated with ethyl ether, collected by filtration and dried for 12 hours under vacuum to get 72 g of 6-arm PEG-amine (10).

White solid, $^1$H-NMR ($CDCl_3$) δ: 2.87 ppm (t, 12H, —$CH_2NH_2$), 3.64 ppm (s, 1818H, PEG backbone,— $OCH_2$—).

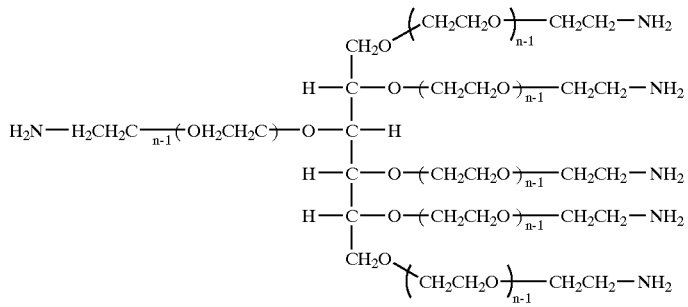

Hereinafter, the formulating methods and kinds of excipients will be described, but the present invention is not limited to them. The representative preparation examples were described as follows.

| Preparation of injection | |
|---|---|
| Compound (10) | 100 mg |
| Sodium metabisulfite | 3.0 mg |
| Methylparaben | 0.8 mg |
| Propylparaben | 0.1 mg |
| Distilled water for injection | optimum amount |

Injection preparation was prepared by dissolving active component, controlling pH to about 6.8–7.6 and then filling all the components in 2 Ml of ample and sterilizing by conventional injection preparation method.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A novel hexa-arm polyethylene glycol (6-arm PEG) compound and its derivatives represented by the following formula (I):

$$\begin{array}{c} \text{(I)} \\ \text{structure} \end{array}$$

wherein, $R_1$ is a hydrogen atom, a hydroxyl group, alkyl group having 1 to 5 carbon atoms, an acrylate group, an acetaldehyde group, an epoxide group, a hydrazide group, a tresylate group, an alkylcarbonyl group or a phenylcarbonyl group having 1 to 10 carbon atoms which substituted by nitro group, primary, secondary or tertiary silane group which substituted by alkyl or alkoxy group having 1 to 5 carbon atoms, glutaric acid group, succinic acid group or $CO(CH_2)_m COONHS$, m is an integer of 2 to 3, n is an integer of 20 to 2500.

2. The compound of claim 1, which is one selected from the group of consisting of 6-arm PEG-succinic acid (6-arm PEG-SA), 6-arm PEG-glutaric acid (6-arm PEG-GA), 6-arm PEG-succimidyl succinate (6-arm PEG-SS), 6-arm PEG-succimidyl glutarate (6-arm PEG-SG), 6-arm PEG-nitrophenyl carbonate (6-arm PEG-NPC), 6-arm PEG-silane, 6-arm PEG-acrylate, 6-arm PEG-hydrazide, 6-arm PEG-tresylate, 6-arm PEG-propion aldehyde, 6-arm PEG-tosylate.

3. A novel hexa-arm PEG compound and its derivatives represented by the following formula (II):

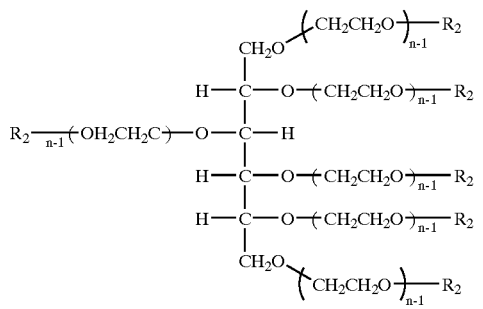

wherein, $R_2$ is a hydrogen atom, a hydroxyl group, an isocyanate group, a maleimide group, a o-pyridyl disulfide group, an alkylsulfonyl, an arylsulfonyl or a vinylsulfonyl group having 1 to 5 carbon atoms, or an alkyl or an alkene group having 1 to 5 carbon atoms which is substituted or not substituted by an amine group, n is an integer of 20 to 2500.

4. The compound of claim 3, which is one selected from the group of consisting of 6-arm PEG-isocyanate,
6-arm PEG-maleimide,
6-arm PEG-orthopyridyl disulfide,
6-arm PEG-vinylsulfone,
6-arm PEG-amine (6-arm PEG-$NH_2$),
6-arm PEG-thiol (6-arm PEG-SH).

* * * * *